(12) United States Patent
Khatchaturov et al.

(10) Patent No.: US 9,017,316 B2
(45) Date of Patent: Apr. 28, 2015

(54) DISTANCE ESTIMATION BETWEEN A FIBER END AND A TISSUE USING NUMERICAL APERTURE MODULATION

(75) Inventors: Arkady Khatchaturov, Haifa (IL); Uri Voitsechov, Moshav Amirim (IL); Igal Koifman, Hadera (IL)

(73) Assignee: Lumenis Ltd. (IL)

( * ) Notice: Subject to any disclaimer, the term of this patent is extended or adjusted under 35 U.S.C. 154(b) by 0 days.

(21) Appl. No.: 13/811,926

(22) PCT Filed: Jul. 25, 2011

(86) PCT No.: PCT/IB2011/053307
§ 371 (c)(1),
(2), (4) Date: Jan. 24, 2013

(87) PCT Pub. No.: WO2012/014145
PCT Pub. Date: Feb. 2, 2012

(65) Prior Publication Data
US 2013/0123769 A1    May 16, 2013

Related U.S. Application Data

(60) Provisional application No. 61/367,790, filed on Jul. 26, 2010.

(51) Int. Cl.
*A61B 18/22* (2006.01)
*A61N 5/06* (2006.01)
*G01B 11/02* (2006.01)
*A61B 17/00* (2006.01)

(52) U.S. Cl.
CPC ....... *A61B 18/22* (2013.01); *A61B 2017/00066* (2013.01); *A61B 2018/2244* (2013.01); *A61N 5/0601* (2013.01); *A61N 2005/063* (2013.01); *G01B 11/026* (2013.01); *A61N 5/06* (2013.01)

(58) Field of Classification Search
CPC ............ A61B 18/18; A61B 3/10; G02B 3/06
USPC ................ 606/4, 9, 12, 16; 359/710; 351/221
See application file for complete search history.

(56) References Cited

U.S. PATENT DOCUMENTS

| | | | | |
|---|---|---|---|---|
| 5,860,967 A * | 1/1999 | Zavislan et al. | ................... | 606/9 |
| 6,717,745 B2 * | 4/2004 | Nemes | .......................... | 359/710 |
| 7,033,350 B2 * | 4/2006 | Bahk | .............................. | 606/12 |
| 7,452,081 B2 * | 11/2008 | Wiltberger et al. | ........... | 351/221 |
| 2007/0135806 A1 * | 6/2007 | Easley | ............................ | 606/16 |
| 2007/0173791 A1 * | 7/2007 | Raksi | ............................... | 606/4 |

FOREIGN PATENT DOCUMENTS

| | | |
|---|---|---|
| DE | 10 2004 025290 | 12/2005 |
| GB | 2 443 318 | 4/2008 |
| WO | 2008/024101 | 2/2008 |

* cited by examiner

*Primary Examiner* — William Thomson
*Assistant Examiner* — Victor Shapiro
(74) *Attorney, Agent, or Firm* — Isus Intellectual Property PLLC

(57) ABSTRACT

A system and method of estimating a distance between the distal end of an optical fiber and treated tissue, to improve treatment efficiency, is provided herein. The estimation is achieved by modulating the numerical aperture of a light beam transmitted through the fiber to receive reflections from the tissue and distinguish them from other reflections in the fiber, and further by calculating the distance by comparing reflection intensities of beams having different numerical aperture values that illuminate the tissue over a very short period, so that tissue and environment conditions do not change much. Distance estimation may be carried out by modulating the treatment beam itself, or by a light beam transmitted between pulses of a pulsed treatment beam.

8 Claims, 5 Drawing Sheets

DISTANCE ESTIMATION BETWEEN A FIBER END AND A TISSUE USING NUMERICAL APERTURE MODULATION

BACKGROUND

1. Technical Field

The present invention relates to optical fibers and more particularly, to laser treatment devices.

2. Discussion of the Related Art

Many non-invasive or minimally invasive treatment methods involve delivering energy to a tissue by irradiating the tissue with a laser beam through an optical fiber. Treatment efficiency depends strongly on the relative position and orientation of the fiber tip in respect to the tissue. However these are very difficult to measure due to the permanent motion of the fiber and permanent changes in the treated tissue and its environment. Hence, currently physicians are in the dark regarding the location of the fiber tip in respect to the treated tissue.

BRIEF SUMMARY

One aspect of the invention provides a method comprising: modulating a numerical aperture of a light beam transmitted through an optical fiber and directed at a target tissue via a distal end of the optical fiber, measuring intensity values of reflections of the light beam reflected from the target tissue and transmitted backward through the optical fiber, and estimating, by comparing intensity values of the reflections associated with two or more numerical aperture values, a distance between the target tissue and the distal end of the optical fiber.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 1 illustrates a reflection of the light beam from an illuminated target tissue, FIGS. 2 and 3 schematically illustrate the transmission of the light beam and measurement of the reflection, and FIGS. 4-6 illustrate various modulation methods of the numerical aperture of the light beam, according to some embodiments of the invention.

Figure 1:
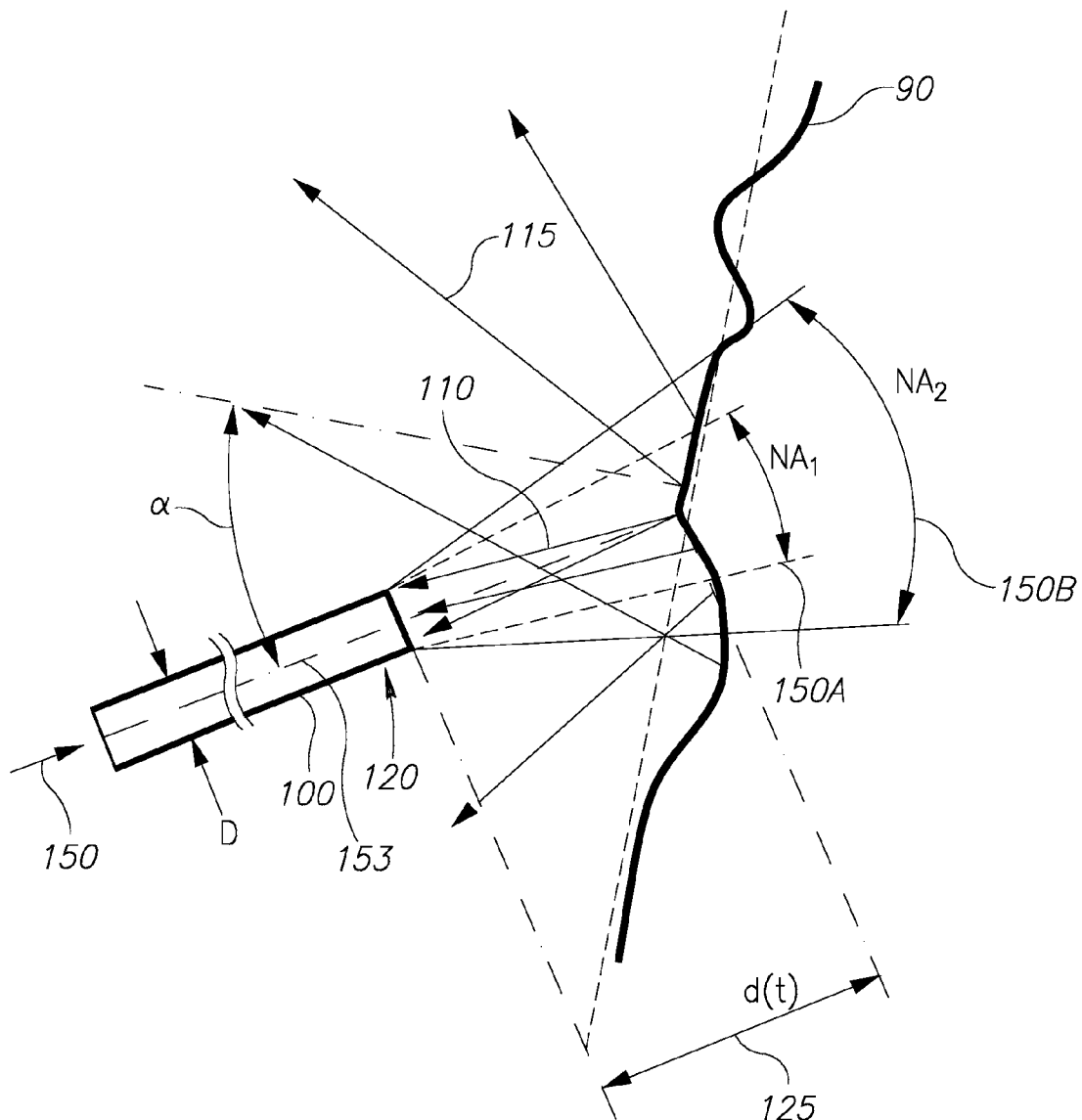
FIGS. 1-6 are high level schematic illustrations of a modulation of the numerical aperture of a light beam, according to some embodiments of the invention.

The drawings together with the following detailed description make apparent to those skilled in the art how the invention may be embodied in practice.

DETAILED DESCRIPTION

Prior to setting forth the detailed description, it may be helpful to set forth definitions of certain terms that will be used hereinafter.

The term "laser" as used herein in this application refers to any type of laser—For example solid state (e.g. Neodymium, Erbium, Holmium, Thulium or Alexandrite), diode (e.g. in various wavelengths, such as in the range 532-1600 nm), gas (e.g. $CO_2$, Argon) or fiber laser (e.g. Neodymium, Erbium, Holmium, Thulium or Alexandrite). Furthermore, laser beams referred to in the application may be continuous, pulsed, Q-switched, or any other temporal pattern.

The term "treatment beam" as used herein in this application refers to an intense laser beam transferred through an optical fiber to treat a target tissue. For example, treatment beam may be a pulsed laser beam or any other laser beam as defined above. The treatment may be ablative or non-ablative, as determined by the beam intensity in respect to a tissue ablation threshold of approximately 10 $kW/cm^2$.

The term "aiming beam" as used herein in this application refers to a light beam with a modulated numerical aperture that is used to estimate the distance between the fiber tip and the target tissue. The aiming beam may be a low energy beam that is not configured to provide treatment or it may be a non-ablative treatment beam, which is modulated (by numerical aperture) at specific periods of its operation to provide the additional function of distance estimation. The aiming beam may be generated e.g. by the same laser source which generates the treatment beam or by another laser source. The aiming beam may be transmitted to the tissue during the treatment or during interruptions in the treatment, such as between pulses of a pulsed treatment beam. The term "measurement beam" as used herein in this application refers to the aiming beam.

The term "light beam" as used herein in this application refers to any light beam transferred through an optical fiber and may refer to either the aiming beam or the treatment beam, as well as to a single beam with temporally varying characteristics, such as to alternately function as a treatment beam and as an aiming beam. Any of the beams referred to in the application may be a laser beam, as defined above.

The term "estimated distance" as used herein in this application refers to an estimation of a distance between the fiber's distal end and the target tissue. As such a distance is difficult to even define (see explanation below), the estimated distance refers to a value reflecting the relative proximity of the distal fiber end and the target tissue, and does not necessarily have a rigorous independent definition.

The term "proximal end of the optical fiber" as used herein in this application refers to the fiber end through which the light beam enters the fiber and propagates towards the distal end of the fiber, which is close to the treated tissue. Reference to measurements carried out at the proximal end relate to the vicinity of the proximal end, e.g. may be carried out by optical equipment coupled to the proximal end, or by equipment receiving beams diverted from the proximal end.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figures 2, 3:
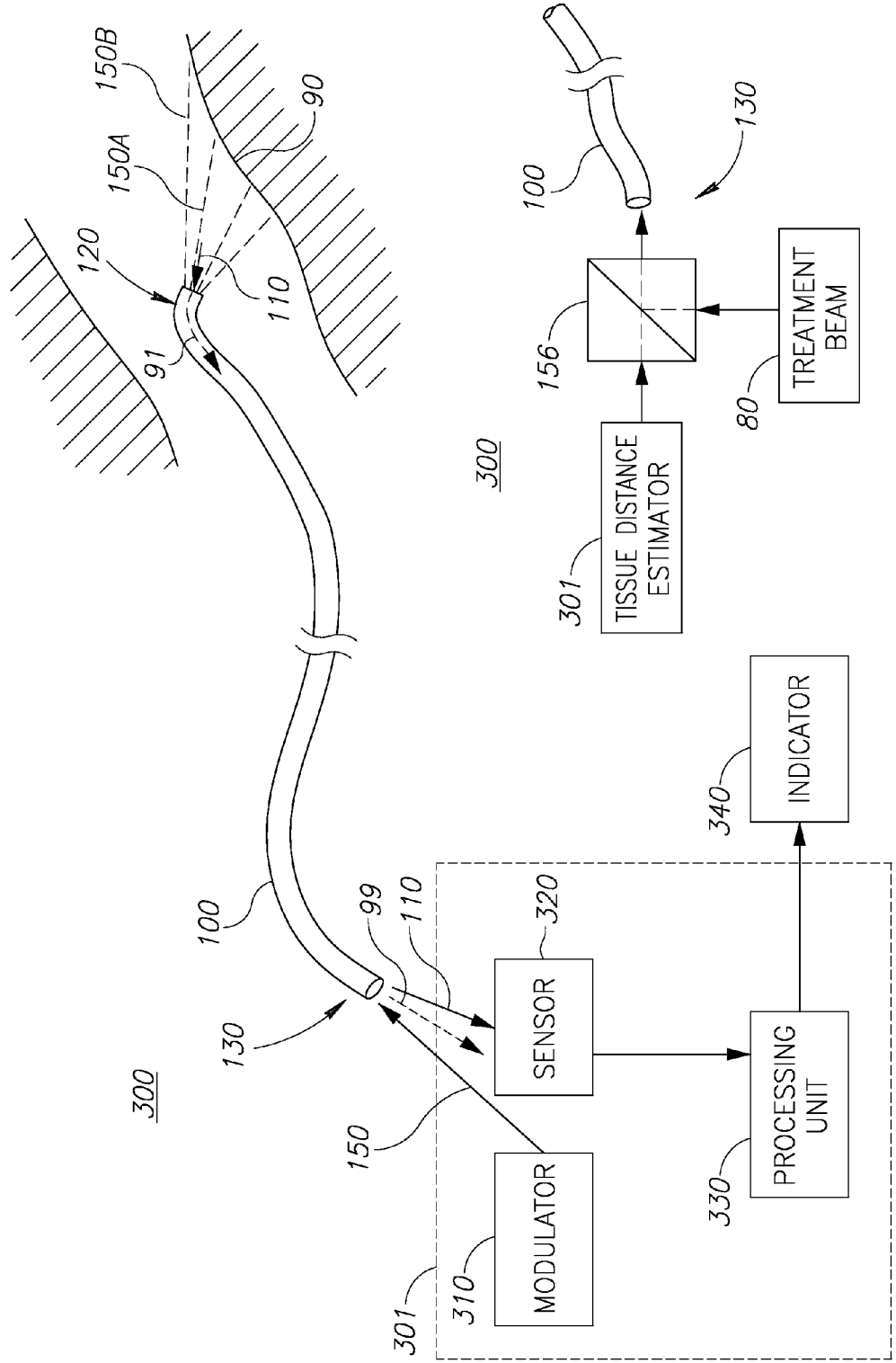
Figure 4:
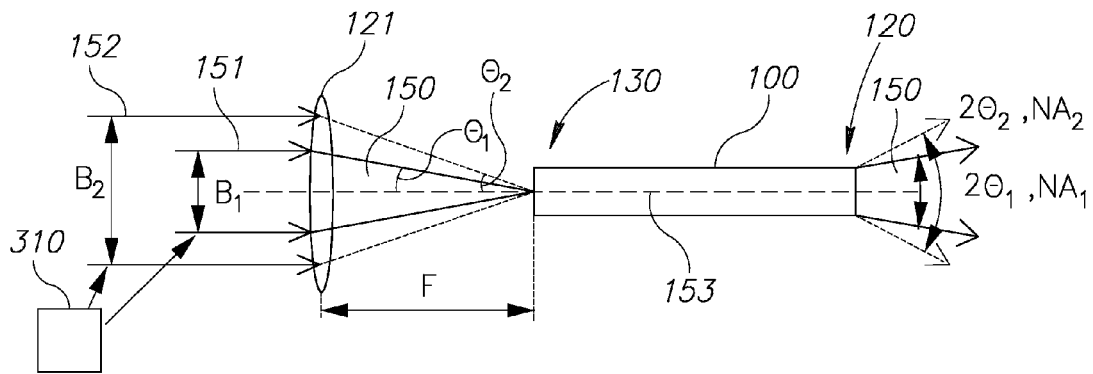
Figure 5A:
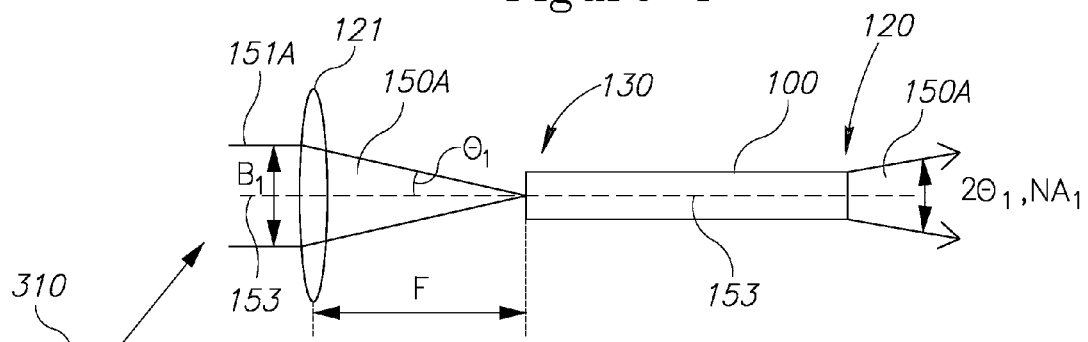
Figure 5B:
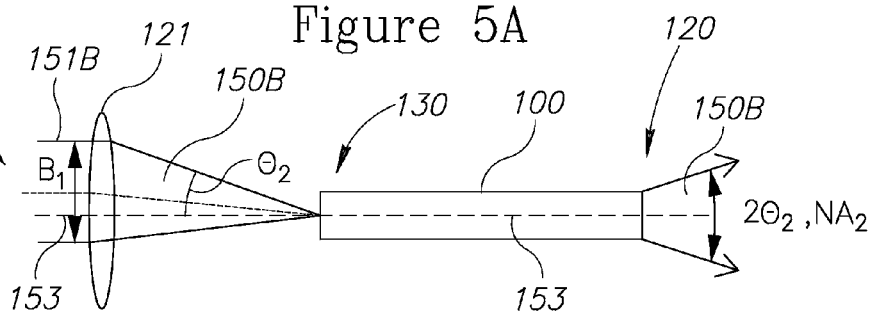
Figure 6:
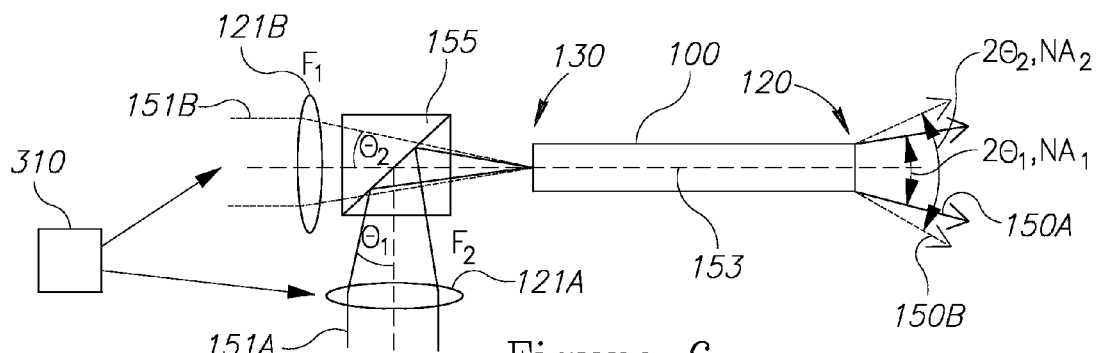

FIGS. 1-6 are high level schematic illustrations of a modulation of the numerical aperture of a light beam 150, according to some embodiments of the invention. FIG. 1 illustrates a reflection 110 of light beam 150 from an illuminated target tissue 90, FIGS. 2 and 3 schematically illustrate the transmission of light beam 150 as an aiming beam and/or as a treatment beam and measurement of reflection 110, and FIGS. 4-6 illustrate various modulation methods of the numerical aperture of light beam 150.

Light beam 150 propagates along optical fiber 100 and illuminates tissue 90. Tissue 90 reflects some of the light (115) away from optical fiber 100, while a part of the light re-enters optical fiber 100 at the fiber's distal end 120 as reflection 110. Reflection 110 is transmitted backward in optical fiber 100 from distal end 120 to the fiber's proximal end 130 and is detected when emerging from proximal end 130. Both entering light beam 150 and reflection 110 may be delivered to and from proximal end 130 (respectively) by optics such as lenses, mirror, reflectors etc. In particular, the measurement of the reflection intensities may be carried out on reflection 110 that is diverted after exiting proximal end 130 and directed to sensor 320.

The current invention presents a method to evaluate a distance 125 of distal end 120 from tissue 90 using reflection 110 as measured at proximal end 130. Distance 125 changes during the manipulation of fiber 100 and is denoted as a function of time by d(t).

Several difficulties impede such a straight forward measurement. (i) Separation of reflection 110 from reflections of light beam 150 from distal and proximal ends 120, 130 (respectively, reflections 91 and 99, FIG. 2) of optical fiber 100 is difficult, as the intensity of reflection 110 is much smaller than those of other reflections 91, 99 in fiber 100. (ii) The reflecting tissue 90 surface geometry is not regular and its optical properties are neither stable nor predictable. Environment transparency, related to debris, bubbles, flushing and other liquids or gas between tissue 90 and fiber distal end 120, changes continuously. These effects are especially imminent in cases of ablative treatment. As fiber 100 moves in respect to tissue 90 and as treatment is applied to tissue, both tissue reflectivity and tissue environment may change strongly and abruptly. (iii) The location (distance d) and orientation (angle α) of fiber 100 in respect to tissue 90 change continuously.

In such working conditions it is not even possible to exactly define a "distance to the target" (i.e. distance 125). In any case it is clear that it could be only somehow averaged distance. The presented invention however, allows a crude estimation of distance 125 from reflection 110. For the stated purpose, diffusive and specular reflections from tissue surface are not differentiated.

Fiber's distal end 120 illuminates tissue 90 within the limits of light beam numerical aperture, NA (in respect to the fiber's optical axis 153). Because the tissue surface is not plane, the angle α and the distance d could be determined only with somewhat uncertainty. The light, coming back to the fiber tip (reflection 110), is reflected from relatively small portion of illuminated tissue surface, so that one may consider averaged values of α and of d from this small portion. The signal S(t) detected at proximal end 130 of fiber 100 is directly proportional to the light intensity I of reflection 110, and may be expressed by the following Equation 1, with D denoting the fiber core diameter.

$$S(t) = \frac{\pi D^2}{4} I \qquad \text{Equation 1}$$

$$= \frac{\pi D^2}{4} \frac{4 p_0 \cos\alpha}{\pi (D + d \cdot NA_\square)^2} \cdot Sct(R, g, \alpha, d)$$

The first term in this expression ($\pi D^2/4$) is the fiber cross section; the second one represents tissue illumination intensity ($4 p_0 \cos(\alpha)/\pi(D+d \cdot NA)^2$), created by optical power $p_0$ irradiated from fiber distal end 120 (assuming uniform angular distribution of the light beam). The last term, $Sct(R,g,\alpha,d)$ is a scattering function, which determines how much energy is reflected toward fiber 100, including all effects of light absorption and scattering by a media between fiber end 120 and tissue surface 90. This function, $Sct(R,g,\alpha,d)$, depends particularly on tissue reflectance R and surface geometry g (each of them includes several parameters). Keeping in mind that almost all of them are variable in time the expression for detected signal could be re-written as Equation 2:

$$S(t) = \frac{F(t)}{\left(1 + \frac{d(t)}{D} \cdot NA(t)_\square\right)^2} \qquad \text{Equation 2}$$

where F(t) is relatively slow arbitrary function of time. It is impossible to use this equation to directly calculate distance 125—d(t), because the signal variation may be caused by unpredictable F(t) function change as well.

However, as the current invention discloses, the problem may be circumvented by modulating the numerical aperture NA of incident light beam 150 in its function as an aiming beam. For the purpose of explanation, the simplest implementation of this principle is discussed in the following, but should not be taken as limiting the current invention. Light beam 150 may be modulated to have periodically alternating values of light beam 150's numerical aperture ($NA_1$, $NA_2$ for light beams 150A, 150B, respectively, neither of which exceeding the fiber numerical aperture). If the period between two consecutive measurement ($S_1$, $S_2$) is short enough to substantially minimize changes in d(t), α(t) and other parameters that determine F(t), then the signal magnitude S(t) varies mainly due to NA variation. Under such conditions, the unknown function F(t) could be eliminated by forming the ratio presented in Equation 3 with minimal level of inaccuracies.

$$\frac{S_1}{S_2} = \left(\frac{1 + \frac{d(t)}{D} \cdot NA_2}{1 + \frac{d(t)}{D} \cdot NA_1}\right)^2 \qquad \text{Equation 3}$$

Equation 3 can be readily solved for the distance d(t), to reach the expression of Equation 4:

$$d(t) = \frac{D \cdot \left(1 - \sqrt{\frac{S_1}{S_2}}\right)}{NA_1 \cdot \sqrt{\frac{S_1}{S_2}} - NA_2} \qquad \text{Equation 4}$$

Clearly, the same principle may be applied to estimate d(t) by using several numerical aperture values $NA_1$, $NA_2$, . . . , $NA_n$, or a continuous range of numerical aperture values, using a analogous calculation to derive d(t) from the reflection intensities.

Considering the light reflected from the both proximal and distal fiber ends (130, 120 respectively) as one of the noise components, the NA modulation significantly improves the signal to noise ratio, because, in principle, only for the light scattered from the tissue (reflection 110) this kind of modulation results in the light intensity modulation.

Thus the NA modulation, in principle, allows solving of all three problems mentioned above. The proposed NA modulation is applicable to both diffusive and specular reflection, because the only difference between diffusive and specular reflection, relates to $Sct(R,g,\alpha,d)$ function which may be cancelled forming Equation 3 allowing reasonable distance estimation.

Hence, the following method achieves the goal of evaluating the distance between fiber distal end 120 and tissue 90 under the treatment using light beam 150 as an aiming beam.

Figure 7:
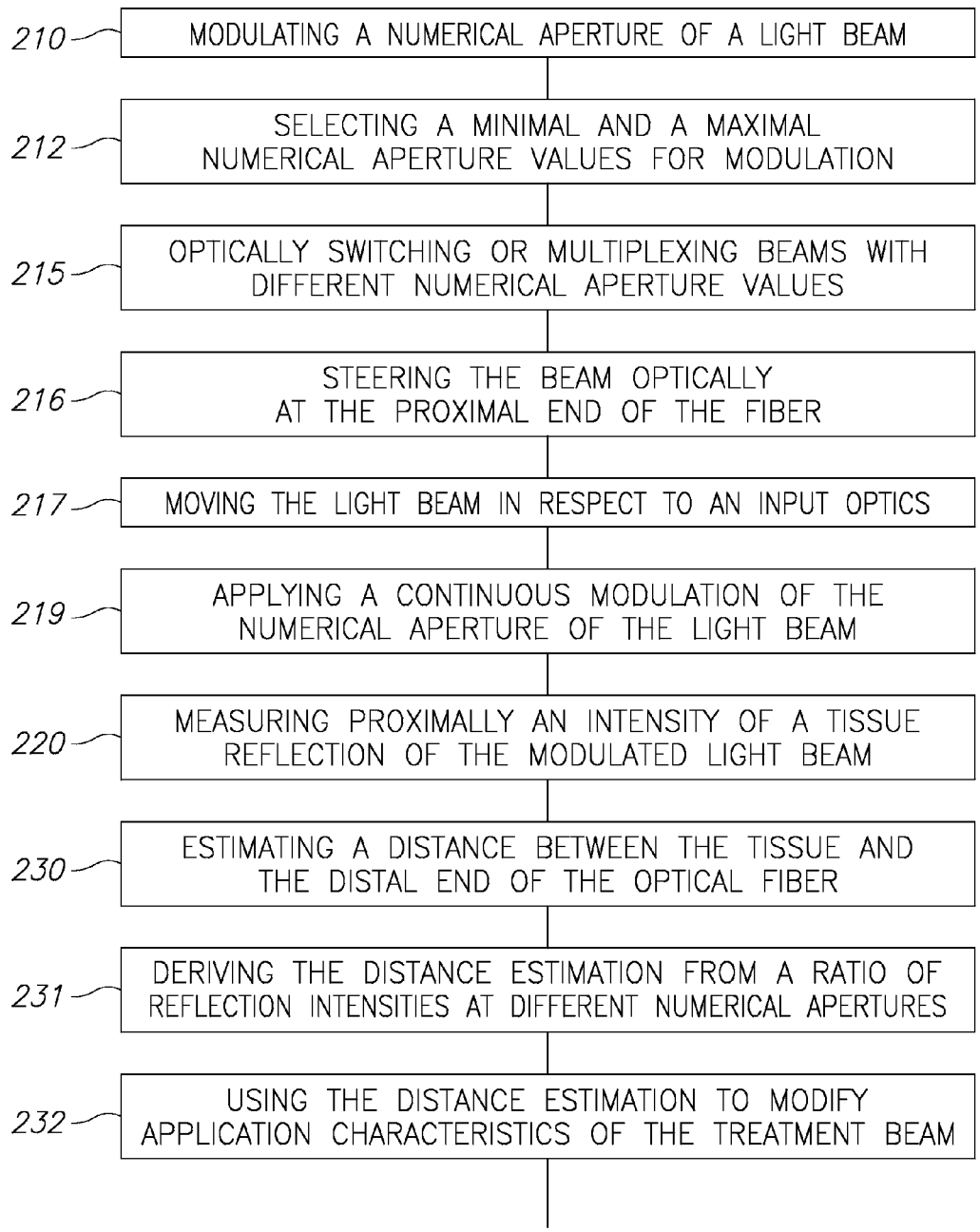
FIG. 7 is a high level flowchart illustrating a method according to some embodiments of the invention.
Figure 7:
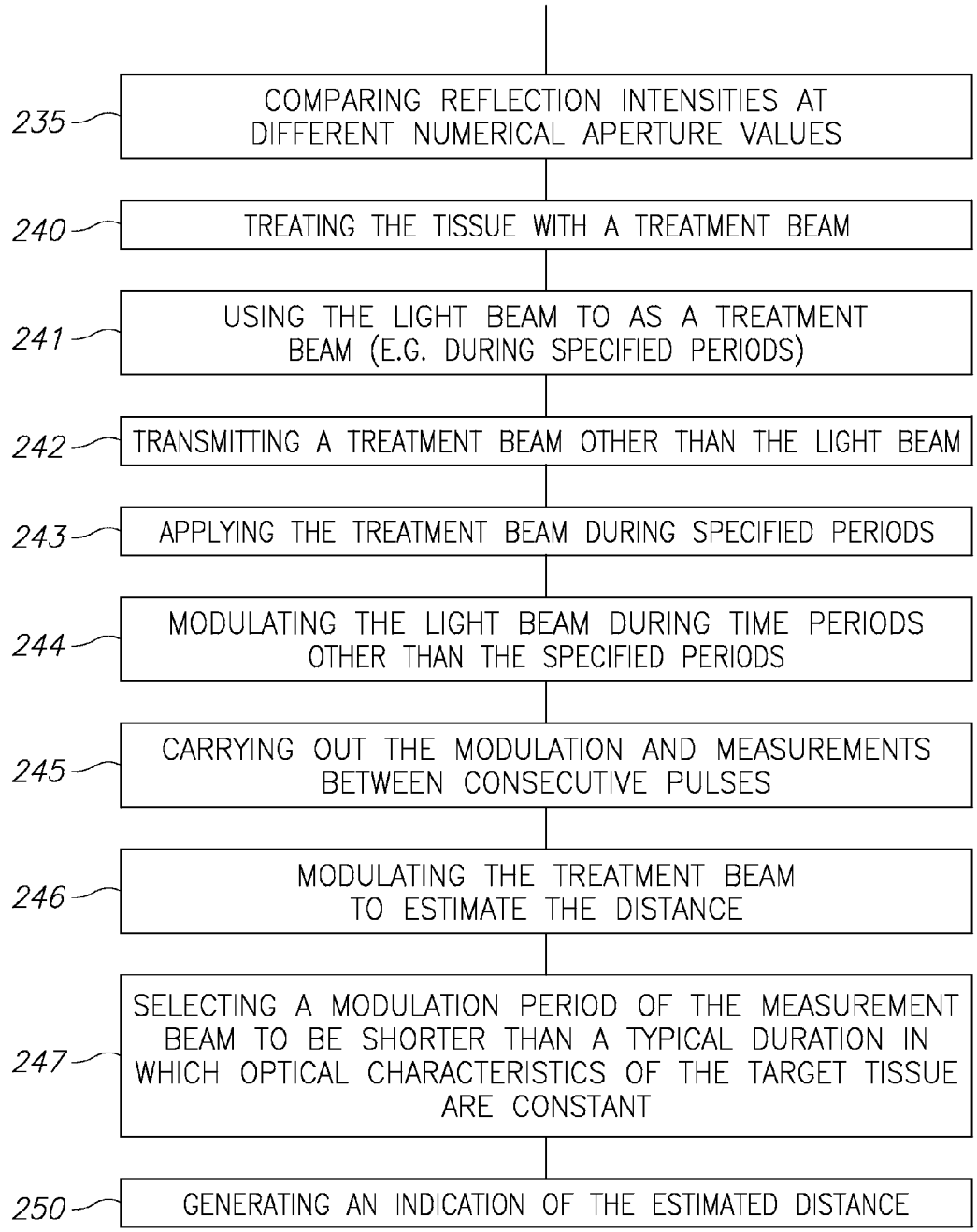

FIG. 7 is a high level flowchart illustrating a method 200 according to some embodiments of the invention. Method 200 generates an estimation of distance 125 from comparing the intensities of light beams 150A and 150B having different numerical aperture values.

Method 200 comprises the following stages: modulating a numerical aperture of a light beam transmitted through an optical fiber and directed at a target tissue via a distal end of the optical fiber (stage 210), measuring intensity values of reflections of the light beam reflected from the target tissue and transmitted backward through the optical fiber (stage 220) to the sensor 320, and estimating (stage 230), by comparing intensity values of the reflections associated with two or more numerical aperture values (stage 235), a distance between the target tissue and the distal end of the optical fiber. Estimation may be carried out according to Equations 3 and 4, or an equivalent equation relating to multiple numerical aperture modulation values or continuous numerical aperture modulation values.

Method 200 may further comprise treating the tissue with a treatment beam (stage 240), for example a laser beam as defined above. The treatment beam may be operated in any mode, for example a pulsed or a continuous mode. Treatment may be carried out by configuring the light beam to apply a specified treatment to the target tissue during specified periods (stage 241), in which the light beam is a treatment beam with specified physical characteristics. Modulating the light beam (stage 210) for the purpose of distance measuring may be carried out during time periods other than the specified periods, in which the light beam is a measurement or an aiming beam (stage 244). For example, the specified periods may be pulses of a pulsed laser, or periods of a high intensity of the light beam. In another embodiment, the treatment beam may be a continuous wave laser and the modulating (stage 210) may be carried out whenever the continuous treatment beam is interrupted or is activated below a given energy threshold.

Treatment may be carried out by transmitting a treatment beam other than the light beam (stage 242), with specified physical characteristics through the optical fiber to apply a specified treatment to the target tissue. The treatment beam may be applied during specified periods (stage 243), and modulating the light beam (stage 210) may be carried out during time periods other than the specified periods, in which the light beam is a measurement or an aiming beam (stage 244). For example, the treatment beam may be a pulsed laser and the modulating (stage 210) may be carried out between pulses of the pulsed laser (stage 245), e.g. between consecutive pulses of the treatment beam, e.g. within 20 msec (corresponding to a 50 Hz pulse frequency).

Method 200 may further comprise selecting a modulation period of the measurement beam (stage 247) to be shorter than a typical duration in which optical characteristics of the target tissue could be considered constant or with minimum level of changes still allowing reliable distance estimation. For example, modulation period may range between 10 and 0.1 msec, corresponding to a modulation frequency between 0.1 and 10 kHz (respectively). During such short periods, neither biological processes nor manipulation of the fiber change the optical characteristics of the target tissue and the distance of the distal end to the tissue. The reflection intensities used for the estimation are those associated with measurements performed close in time, in particular consecutive measurements.

The temporal relation of the modulated light beam and the treatment beam may depend on the type of the treatment. For example, an ablative treatment, causing much tissue damage, may require the modulation, measurement and distance estimation (stages 210, 220, 230) to be carried out only when the immediate treatment effects subside. In case of a non-ablative treatment, the modulation, measurement and distance estimation (stages 210, 220, 230) may be carried out even during treatment (e.g. by modulating the treatment beam, stage 246, and measuring reflection intensities of the treatment beam at different numerical apertures, and estimating the distance from these values), as long as the treatment does not drastically change the optical characteristics of the target tissue and its surroundings.

In embodiments, the distance estimation (stage 230) may be derived from a ratio of reflection intensities at different numerical apertures, e.g. under an assumption of constant optical characteristics, or minimal optical characteristics changes, of the target tissue during the time between these two measurements (stage 231). The ratio must be configured by using the values measured close enough in time.

Modulating the aiming beam (stage 210) may be such that the modulated aiming beam exhibits at least two numerical aperture values (stage 212) including, for example, approximately a maximal numerical aperture of the fiber (e.g. ca. 0.22) and approximately a minimal, diffraction limited numerical aperture (e.g. in the order of magnitude of $\lambda/D$ with $\lambda$ denoting the light wavelength and D denoting the fiber core diameter). Modulation (stage 210) may be binary and carried out by two alternating numerical aperture values. In embodiments, modulation (stage 210) is carried out continuously over a specified range of numerical apertures (stage 219) within a maximal possible range between a numerical aperture of the optical fiber and a diffraction-limit of the optical fiber.

Modulation (stage 210) may be carried out by (i) optically switching or multiplexing light beams exhibiting different numerical aperture values prior to entering the fiber (stage 215) or (ii) beam steering implemented by moving input optics, such as one or more lenses, filters or reflectors along the optical path of the between the laser source and the proximal end of the fiber (stage 216) or moving the light beam in respect to the input optics, in a direction perpendicular to an optical axis of the input optics (stage 217). Additional methods such as beam steering using a grating may be used to modulate the numerical aperture values of the light beams (e.g. by changing beam width—FIG. 4). A shutter and a chopper may also be used to switch (if needed) the combined beams.

Method 200 may further comprise generating an indication of the estimated distance (stage 250), such as an acoustic indication, a visual indication (textual, graphical or both), and a vibratory indication.

The distance estimation (stage 230) may be used to modify the specified physical characteristics and/or the specified periods of the treatment beam application (stage 232).

Method 200 may be implemented by a tissue distance estimator 301 and a tissue treatment system 300 illustrated in FIGS. 2-6.

FIGS. 2 and 3 schematically illustrate the transmission of light beam 150 as the aiming beam and measurement of reflection 110, and FIGS. 4-6 illustrate various modulation methods of the numerical aperture of light beam 150.

Tissue distance estimator 301 operates in an optical fiber system that comprises light beam 150 emitted onto tissue 90 from distal end 120 of optical fiber 100. Tissue distance estimator 301 is associated with proximal end 130 of fiber 100 and comprises a modulator 310, a sensor 320, and a processing unit 330: Modulator 310 is arranged to modulate a numerical aperture of light beam 150 transmitted through optical fiber 100 and directed at target tissue 90, sensor 320 is arranged to measure intensity values of reflections 110 of light beam 150 coming from target tissue 90 and passing backward through optical fiber 100, and processing unit 330 is arranged to receive the intensity measurements from sensor 320 and estimate, by comparing intensity values of reflections 110 associated with two or more numerical aperture values, distance 125 between tissue 90 and distal end 120 of optical fiber 100. Estimated distance 125 may serve as a proxy for the user of the system for enhancing the effective operation of the system.

Modulator 310 may control a collimated input beam 152 (FIG. 4), to yield an input beam 151 with a varying beam diameter $B_1$, $B_2$ on input optics 121 (e.g. lens), resulting in different numerical aperture values of resulting light beam 150 at the focal point at the entrance to fiber 100.

Alternatively, modulator 310 may comprise a beam steering device (not shown), arranged to periodically change an incidence location of light beam 150 upon input lens optics 121 of the optical fiber system at proximal end 120 of fiber 100, to modulate the numerical aperture of light beam 150. The beam steering device, controlled by modulator 310, may move collimated light beam 151 upon the face of input lens 121 to change the range of entrance angles of light beam 150 into fiber 100. FIGS. 5A and 5B illustrate two positions of the beam steering device—in FIG. 5A incoming beam 151A is centered around optical axis 153 resulting in light beam 150A, while in FIG. 5B incoming beam 151B, e.g. of the same diameter B, is off-center in respect to optical axis 153, resulting in a larger entrance angle $\theta_2 > \theta_1$ and a larger numerical aperture of light beam 150 due to the fiber axial symmetry.

In one embodiment of the system, modulator 310 may comprise at least two laser sources emitting beams 151A, 151B with different numerical apertures $NA_1$, $NA_2$ through input optics 121A, 121B (e.g. lenses with different focal lengths $F_1$, $F_2$) respectively. A combiner 155 and an optical switch (not shown) that is controlled by modulator 310 may be used to provide alternately beams 151A, 151B as sources for light beams 150A, 150B respectively, having different numerical apertures, denoted in FIG. 6 by angles $\theta_1$ and $\theta_2$.

Processing unit 330 may be arranged to derive the distance estimation from a ratio of reflection intensities at different numerical aperture. The optical characteristics of the target tissue may be considered more or less constant during the modulation period and measurements. The time constants for the modulating and the measuring may be selected to match the conditions under which Equations 3 and 4 were derived.

Tissue distance estimator 301 may be part of a tissue treatment system 300, that further comprises a treatment beam laser 80, arranged to deliver energy via optical fiber 100 to target tissue 90. In this case, estimated distance 125 may serve as a proxy for the physician to enhance treatment efficiency. Light beam 150 and treatment beam 80 may be separate beams and introduced into fiber 100 by combiner 156 (FIG. 3), or light beam 150 and treatment beam 80 may origin from the same source, e.g. from the same laser source. For example—the treatment may be applied in pulses with specific physical characteristics, while light beam 150 as measurement beam may be applied between the pulses with different physical characteristics. In another example, the treatment beam itself may be modulated and used as the measurement beam, for example in the case of a continuous wave treatment beam.

Modulator 310 and sensor 320 are arranged to carry out the modulation and the measurement (respectively) during interruption periods of treatment laser 80. Treatment laser 80 may be pulsed, and modulator 310 and sensor 320 may be arranged to carry out the modulation and the measurement (respectively) between pulses of treatment laser 80.

Light beam 150 used by tissue distance estimator 301 may be produced by treatment laser 80 and be, e.g. of low intensity, in contrast to the high intensity treatment beam.

Modulator 310 and sensor 320 are arranged to carry out the modulation and the measurement (respectively) during lasing interruptions of the laser 80. The period between consecutive measurements must be shorten so that F(t) would change as little as possible. Furthermore, the measurement period may be selected in relation to the applied treatment and the operationally required frequency of distance estimation.

Tissue treatment system 300 may further comprise an indicator 340 arranged to indicate the estimated distance by at least one of: an acoustic indication, a visual indication, and a vibratory indication.

The proposed modulation of numerical aperture allows differentiating the weaker reflection 110 that arrives to sensor 320 from the more intense reflections 91 and 99. Moreover, by comparing successive reflections from target tissue 90 that result from light beams of varying numerical aperture, a crude assessment of distance 125 between target tissue 90 and distal fiber end 110 may be achieved. The invention utilizes the fact that mainly tissue reflections 110 respond differently to different numerical aperture values of light beam 150.

In the above description, an embodiment is an example or implementation of the invention. The various appearances of "one embodiment", "an embodiment" or "some embodiments" or "embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention.

What is claimed is:

1. A tissue treatment system to treat target tissue comprising:
   a pulsed treatment laser, arranged to treat the target tissue by delivering energy via an optical fiber to the target tissue, the optical fiber having a proximal end and a distal end; and
   a tissue distance estimator, the tissue distance estimator comprising:
   a modulator positioned at the proximal end of the optical fiber and arranged to modulate a numerical aperture of a light beam transmitted through the optical fiber and directed at the target tissue via the distal end of the optical fiber;
   a sensor positioned at the proximal end of the optical fiber and arranged to measure intensity values of reflections of the light beam reflected from the target tissue and transmitted backward through the optical fiber; and
   a processing unit arranged to receive the intensity measurements from the sensor and estimate, by comparing intensity values of the reflections associated with two or more numerical aperture values, a distance between the target tissue and the distal end of the optical fiber;
   and;
   wherein the modulator and the sensor are arranged to respectively carry out the modulation and the measurement between pulses of the treatment laser.

2. The tissue treatment system of claim 1, further comprising a source of the light beam other than the treatment laser.

3. The tissue treatment system of claim 1, further comprising an indicator arranged to indicate the estimated distance by at least one of: an acoustic indication, a visual indication, and a vibratory indication.

4. The tissue treatment system of claim 1, wherein the processing unit is further arranged to modify physical characteristics and treatment periods of the treatment beam according to predefined rules.

5. The tissue treatment system of claim 1, wherein the modulator comprises at least two laser sources emitting beams with different numerical apertures and an optical switch arranged to alternate the beams as sources for the light beam.

6. The tissue treatment system of claim 1, wherein the modulator comprises a beam steering device, arranged to periodically change an incidence location of the light beam in respect to an optical axis of an input optics of the optical fiber at the proximal end of the fiber, to modulate the numerical aperture of the light beam.

7. The tissue treatment system of claim 1, wherein the modulator is arranged to change an incidence beam diameter of the light beam upon an input optics at the proximal end of the fiber, to modulate the numerical aperture of the light beam.

8. The tissue distance estimator of claim 1, wherein the processing unit is arranged to derive the distance estimation from a ratio of reflection intensities at different numerical apertures.

* * * * *